US008334751B2

(12) United States Patent
Azevedo et al.

(10) Patent No.: US 8,334,751 B2
(45) Date of Patent: *Dec. 18, 2012

(54) SYSTEMS AND METHODS FOR MANAGING INVENTORY OF ITEMS HELD IN A CABINET USING RADIO FREQUENCY IDENTIFICATION (RFID)

(75) Inventors: John Azevedo, San Marcos, CA (US); Jeffrey Zhu, Westport, CT (US); Eric Mikuteit, San Diego, CA (US); Jun Liu, San Diego, CA (US)

(73) Assignee: Neology, Inc., Poway, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/174,684

(22) Filed: Jun. 30, 2011
(Under 37 CFR 1.47)

(65) Prior Publication Data

US 2012/0019358 A1 Jan. 26, 2012

Related U.S. Application Data

(63) Continuation of application No. 12/420,002, filed on Apr. 7, 2009, now Pat. No. 7,994,897, which is a continuation of application No. 11/692,101, filed on Mar. 27, 2007, now Pat. No. 7,518,516.

(60) Provisional application No. 60/743,823, filed on Mar. 27, 2006, provisional application No. 60/743,825, filed on Mar. 27, 2006.

(51) Int. Cl.
*B60R 25/00* (2006.01)

(52) U.S. Cl. .......... 340/5.73; 340/5.1; 340/5.2; 340/5.3; 340/5.4; 340/5.5; 340/10.1; 340/10.2; 340/10.3; 340/10.4; 340/10.5; 340/572.1; 340/572.2; 340/572.3; 340/572.4; 340/572.5; 235/375; 235/377; 235/380; 235/384; 235/385

(58) Field of Classification Search ............ 340/5.1–5.6, 340/10.1–10.5, 572.1–572.9; 700/231; 235/375–385

See application file for complete search history.

(56) References Cited

U.S. PATENT DOCUMENTS 5,689,238 A 11/1997 Cannon et al.
(Continued)

FOREIGN PATENT DOCUMENTS

EP 1598748 A2 11/2005
(Continued)

OTHER PUBLICATIONS

Extended European Search Report and Opinion issued by the European Patent Office for EP 07759508.0 on Aug. 4, 2011 (10 pages).

*Primary Examiner* — George Bugg
*Assistant Examiner* — Ojiako Nwugo
(74) *Attorney, Agent, or Firm* — Procopio Cory Hargreaves & Savitch LLP; Noel C. Gillespie

(57) ABSTRACT

A RFID cabinet comprises a cabinet structure and one or more drawers or shelves. Chambers are formed within the cabinet to house the one or more drawers or shelves. An RFID scanner is configured to scan items tagged with RFID tags in the chambers via one or more antennas. The antennas can include transmit and receive antennas or antennas configured to perform both transmit and receive functions. The drawers can have a access cover, or lid that can be controlled so as to control access to the drawer. The scanner can be configured to perform inventory control for the tagged items.

9 Claims, 11 Drawing Sheets

Cover in locked position

U.S. PATENT DOCUMENTS

| | | |
|---|---|---|
| 6,424,260 B2 | 7/2002 | Maloney |
| 7,129,840 B2 | 10/2006 | Hull et al. |
| 7,295,120 B2 | 11/2007 | Waldner et al. |
| 7,336,174 B1 | 2/2008 | Maloney |
| 2003/0117281 A1* | 6/2003 | Sriharto et al. ............ 340/568.1 |
| 2003/0164401 A1 | 9/2003 | Andreasson |
| 2004/0212542 A1 | 10/2004 | Rahim |
| 2005/0113970 A1* | 5/2005 | Holmes et al. ................ 700/242 |
| 2005/0116593 A1 | 6/2005 | Berger |
| 2005/0150102 A1 | 7/2005 | Bosco et al. |
| 2006/0022827 A1 | 2/2006 | Higham |
| 2006/0102718 A1 | 5/2006 | Kajino et al. |
| 2007/0103304 A1 | 5/2007 | Newton et al. |

FOREIGN PATENT DOCUMENTS

| | | |
|---|---|---|
| EP | 1710380 A1 | 10/2006 |
| WO | 2004014189 A1 | 2/2004 |
| WO | 2004068871 A2 | 8/2004 |
| WO | 2005073492 A1 | 8/2005 |

\* cited by examiner

Cover unlocked

Cross Section View from the end of tag

Floor Plan view

SYSTEMS AND METHODS FOR MANAGING INVENTORY OF ITEMS HELD IN A CABINET USING RADIO FREQUENCY IDENTIFICATION (RFID)

RELATED APPLICATIONS INFORMATION

This application claims priority as a continuation under 35 U.S.C. 120 to U.S. patent application Ser. No. 12/420,002, filed Apr. 7, 2009, and entitled "Systems and Methods for Managing Inventory of Items Held in a Cabinet Using Radio Frequency Identification (RFID)," which in turn claims priority as a continuation under 35 U.S.C. 120 to U.S. patent application Ser. No. 11/692,101 (now U.S. Pat. No. 7,518,516), filed Mar. 27, 2007, and entitled "Systems and Methods for Managing Inventory of Items Held in a Cabinet Using Radio Frequency Identification," which in turn claims priority under 35 U.S.C. §119(e) to U.S. Provisional Patent Application No. 60/743,823, filed Mar. 27, 2006, entitled "Resonant Chamber for RFID Systems, and to U.S. Provisional Patent Application No. 60/743,825, filed Mar. 27, 2006, entitled "RFID Systems Employing Harmonic Reception," all of which are incorporated herein by reference in their entirety as if set forth in full.

BACKGROUND INFORMATION

1. Field

The embodiments described herein are related to Radio Frequency Identification (RFID), and more particularly to managing inventory for items stored in cabinets.

2. Background

Inventory control and asset tracking of items within a container (such as cabinet or shelf) are currently managed by various modes such as barcode, item count, honor system, and/or a check in/out sheet. The problem with these systems is that they require human intervention, which is inherently flawed and prone to errors. Generally a perpetual audit is implemented to correct the errors however this is resource intensive and does not identify the root cause of the problem.

For example, prescription medications in a hospital are often stored in cabinets that can be wheeled from patient room to patient room. Accurate inventory control of the medications is important to ensure that the medications are not stolen and to be sure that they are restocked when needed. The flaws with conventional inventory control processes can lead to significant consequences if inventory is removed without permission or not restocked. Moreover, it is outside the ability of conventional techniques to ensure that the correct medication in the correct amount is provided to each patient.

As a result, current solutions, e.g., barcodes, have been replaced by RFID solutions. An RFID solution can comprise RFID stickers or labels, i.e., a sticker or label that includes and RFID tag, affixed to the inventory items, e.g., bottles. Information related to each item can then be stored in the tag and read by a scanner. For example, the tag's unique identification number can be associated to a central database and, e.g., used in tracking certain items or for other purposes. In order to read the tags, a number of antennas are placed within the cabinet. The antennas are interfaced with the scanner, which can be in, or on the cabinet. The scanner sends interrogation signals via the antennas to the tags requesting the information stored thereon. The tags respond with a signal that is also picked up by the antennas and forwarded to the scanner.

It will be understood that the tags can be active or passive tags. Active tags have a battery on board; however, conventional active tags are bulky, in part due to the battery, and therefore are not optimal for many cabinet applications. Passive tags on the other hand do not include a battery and can therefore be made quite small and can therefore be preferable for cabinet applications. Passive tags are powered via the interrogation signals received form the scanner.

In some instances, different antennas can be used to transmit interrogation signals and to receive the tag replies. In general, however, conventional RFID solution employ a combined transmit and receive antenna system for simplicity, reduction of antennas and to follow the traditional concept that the most effective receive antenna is the one that is capable of illuminating the tag. In any event, the antennas must be placed so as to increase the likelihood that the interrogation signals can be received by all tags, and to ensure that all of the responses can be received and deciphered.

Conventional cabinet solutions employ a conductive chamber design to contain the RF energy associated with the interrogation signals within the chamber for increased field strength and spatial diversity; however, many such conventional designs can suffer from poor results obtained due to the static nature of the interrogations. In an application where the field is static, a tag may lie in a RF null created by multipath, resulting in a failed interrogation. Since most cabinet solutions are designed for asset tracking or secure inventory control, a form of a lock is used to secure the contents during the RFID interrogation and when not in use to prevent fraudulent activity. Since access to the cabinet's contents is prohibited during a RFID interrogation, the cabinet's doors and/or drawers need to be locked resulting in a static read of the cabinet's contents. Accordingly, conventional cabinet applications by design are static during the RFID interrogation process and suffer from occasional failed interrogation due to a tag being located within a null.

Further, many conventional solutions use the traditional combined transmit/receive antenna configuration. This configuration works well in traditional applications where the scanner antenna radiates into open space and objects are in the far-field region for minimum scanner antenna detuning. Farfield is described as a boundary region where the angular field distribution is essentially independent of distance from the source; however, in applications where the tag is in the near-field, such as in cabinet applications, the traditional combined transmit/receive antenna approach and combined transmit and receive systems suffer greatly from the scanner's inability to listen to the tag's response.

As tagged product enters the scanner's near-field region, it has an adverse effect on the scanner's antenna tuning resulting in reduced scanner receiver sensitivity. This results in scanner antenna detuning and presents a challenge for the scanner's receiver in terms of energy reflected back into the scanner receiver competing with energy reflected back by the tagged items.

Further, as will be understood, typical RFID systems require the scanner to receive a backscatter signal from the tag while transmitting. Simultaneous transmission and reception causes high levels of RF energy to enter the receiver, ultimately limiting the receiver sensitivity. Existing system designs attempt to solve this problem by either minimizing the signal reflections back into the receiver or by using separate transmit and receive antennas. Minimizing signal reflections via component selection has practical limitations. Using separate antennas increases the system cost and requires additional space.

Still further, RF signal propagation in contained environments is not well defined, with huge amplitude variations in resonant versus null locations within a drawer or chamber.

When RFID tags are placed in a chamber's null locations, the tags cannot be powered and cannot be read/interrogated, ultimately causing the overall application to fail.

Another problem exist when a tag is in its minimum field strength (such as between two transmitting antennas) with respect to its ability to turn on and participate in the interrogation. When this occurs the scanner may be unable to detect the tags faint responses resulting in a failed interrogation. This is a common problem in a high product/tag density application where high concentration of items exists within the RF Tx and Rx paths.

Another problem with conventional solutions occurs when the items being tracked include large amount of liquids. Conventional RFID cabinet systems typically use the electric field to communicate to beam powered RFID tags. Depending on frequency used, some frequencies can be greatly attenuated by liquid items within the cabinet resulting in failed interrogation due to insufficient field strength.

Still another problem is that the tags have an effective area that is much larger then the real area and is normally at least IA wavelength of the frequency. RFID application in particular are very sensitive to this due to the fact that the RFID tags are typically place on various items that can greatly reduce the tags efficiency due to intrusion of its effective area. This problem is compounded in applications that do not adhere to any item discipline since the item itself can come into contact with the RFID tag.

These and other problems/issues can significantly reduce the effectiveness of inventory tracking using RFID enabled cabinets.

SUMMARY

A RFID cabinet comprises a cabinet structure and one or more drawers or shelves. Chambers are formed within the cabinet to house the one or more drawers or shelves. An RFID scanner is configured to scan items tagged with RFID tags in the chambers via one or more antennas. The antennas can include transmit and receive antennas or antennas configured to perform both transmit and receive functions. The drawers can have an access cover, or lid that can be controlled so as to control access to the drawer. The scanner can be configured to perform inventory control for the tagged items.

In one aspect, the scanner can be configured to perform a dynamic scan of the tagged items while a drawer is being opened or closed. For example, when access to a drawer is requested, e.g., by activating an unlocking mechanism or inputting an access request that is relayed to the scanner, the scanner can perform a static scan of the tagged items in that drawer. Once the static scan is completed, access to the drawer can be granted and the drawer can be pulled out either manually or automatically. As the drawer is being removed, the scanner can continue to scan the tagged items. Once this dynamic scan is complete, then the access lid can be unlocked and opened to gain access to the scanned items.

When the lid is closed, the scanner can be configured to start scanning the tagged items as the drawer is being pushed back in, either manually or automatically. Once the drawer is all the way back in, then the scanner can perform another static scan.

In another aspect, antennas within a chamber can be configured so that they can be dynamically switched between transmit and receive functions in order to ensure that no tagged items within the chamber are missed. In such embodiments, the scanner has separate transmit and receive paths and a switching network is included to switch the antennas between the transmit and receive paths as required.

In another aspect, receive antennas can be strategically placed between transmit antennas within a chamber in order to ensure that no tagged items are missed.

In another aspect, the chambers can be configured as resonant chambers configured to resonate at the frequencies being used. This can be achieved via the careful selection of chamber dimensions, the use of metallic chamber material, the use of absorbers, and the strategic placement of antennas.

In another aspect, harmonic frequencies can be used by the tags when responding to interrogations from the scanner.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which.

DETAILED DESCRIPTION

The systems and methods described below are directed to what has been termed herein as RFID cabinet applications; however, it will be apparent that the systems and methods described below can be applied to any system in which a plurality of items being tracked or interrogated are located within a confined space. It will also be apparent that certain aspects of the embodiments described below are not necessarily limited to cabinet or confined space applications. Thus, it will be understood that the embodiments described below are by way of example only and are not intended to limit the systems and methods described herein to particular applications unless such a limitation is expressly indicated.

Figure 1:
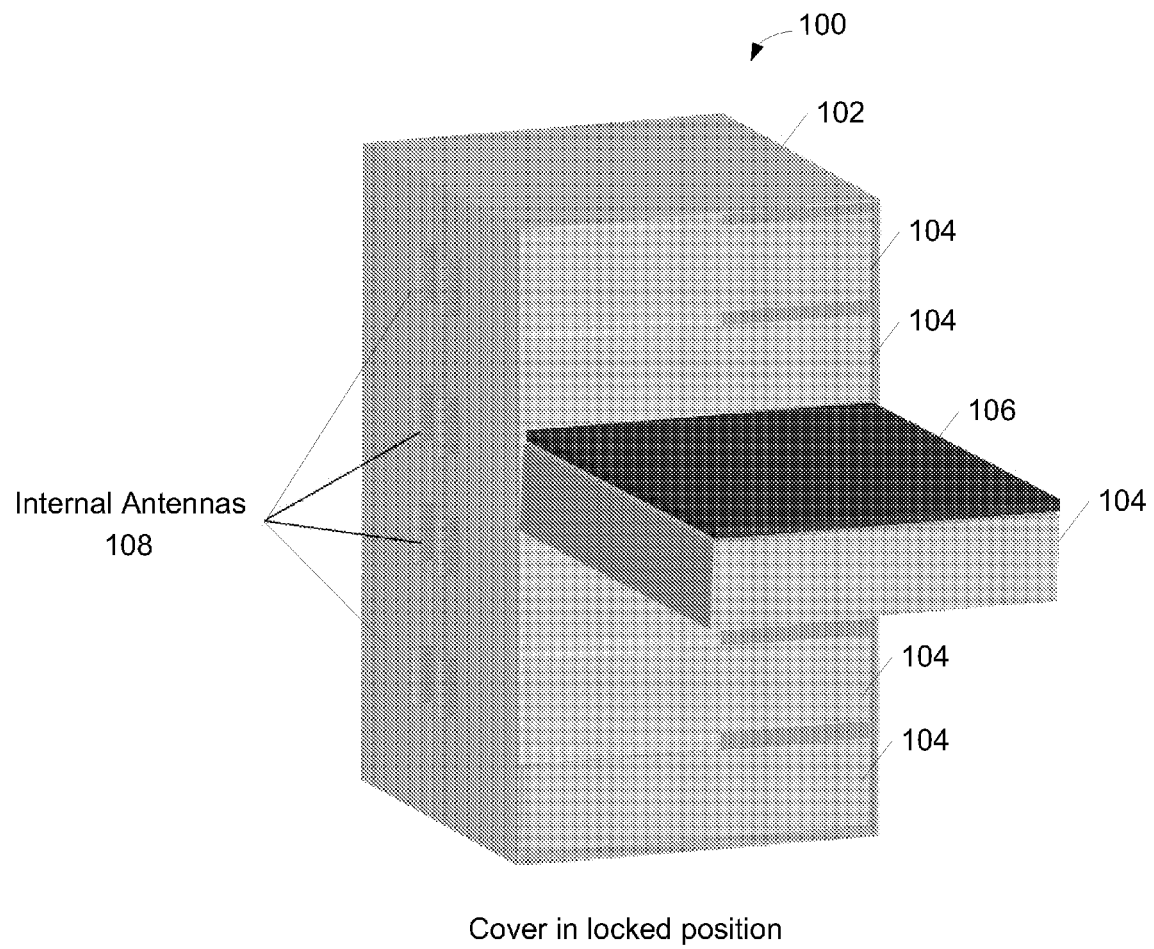
FIGS. 1 and 2 are diagrams illustrating an example cabinet that is configured for RFID inventory tracking in accordance with one embodiment.
Figure 2:
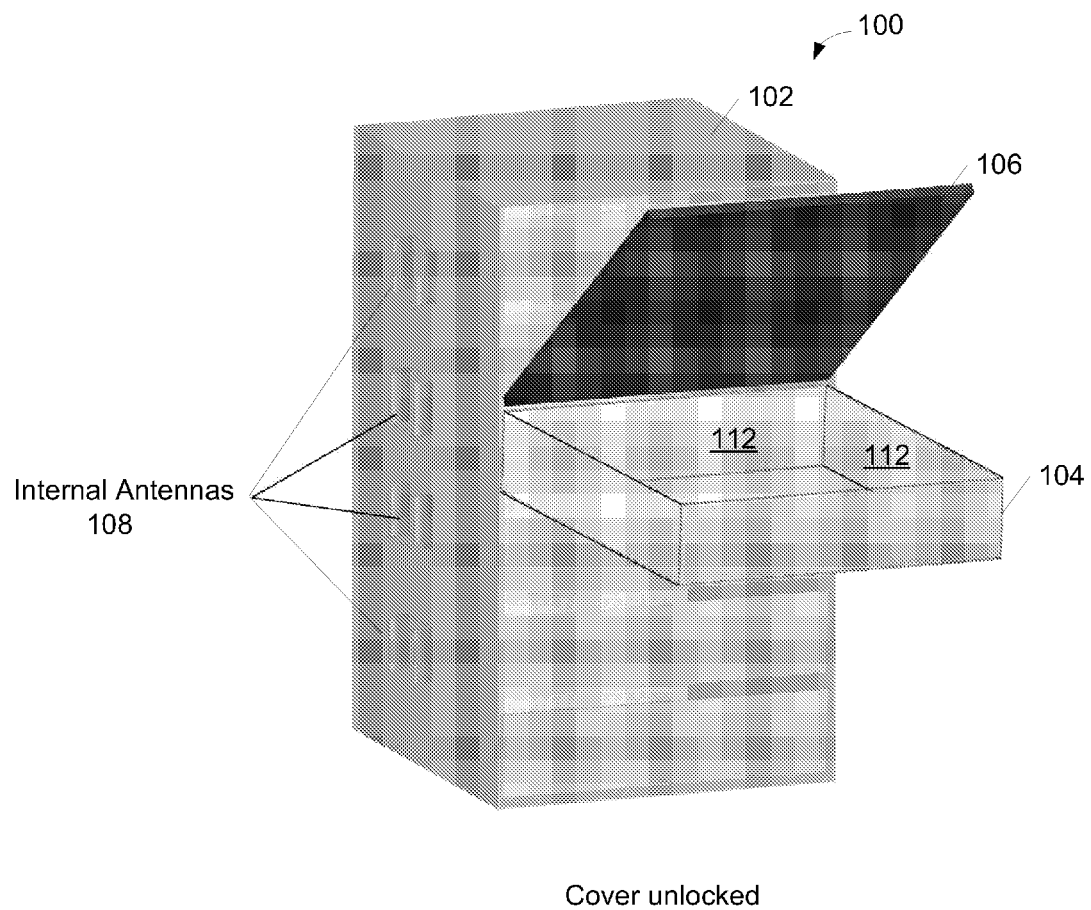

FIGS. 1 and 2 are diagrams illustrating an example cabinet 100 that is configured for RFID inventory tracking in accordance with one embodiment. Cabinet 100 can be configured to track a plurality of items such as medications, tools, jewelry, or any other sensitive items. Cabinet 100 comprises a housing or enclosure 102 configured to house a plurality of drawers 104. It will be understood that more or less drawers can be included and that the drawers can be of the same or different dimensions. Further, more than on drawer per row can also be included.

Each drawer 104 can comprise a lid 106. Lid 106 can, for example be used to secure the contents of individual drawers. Thus, when a drawer 104 is shut, lid 106 can be locked, or otherwise secured. When a drawer 104 has been slid forward, lid 106 can be unlocked and opened as illustrated in FIG. 2. With lid 106 opened, inner walls 112 of drawer 104 are visible in FIG. 2. It will be understood that in certain embodiments, each drawer 104 can comprise multiple chambers separated by walls or partitions.

As noted above, conventional cabinet solutions can suffer from poor results due to the static nature of the read process. In certain embodiments, a dynamic read process can be incorporated and combined with the more traditional static read process to improve performance. As will be explained, the dynamic read can occur as drawer 104 is being opened and closed. In this manner, implementations of such embodiments can combine the security features of a cabinet system as described above, i.e., controlled access via a locking system that can include, e.g., lid 106, with the read reliability of a dynamic RFID interrogation. This is accomplished by using a cabinet system that contains one to many drawers 104 with antennas 108 in a fixed position within the main cabinet structure 102 that interrogate the contents of drawer 104 while drawer 104 is being opened and/or closed by the user. To prevent illicit activity, such as removing an item after it is interrogated, access cover 106 can be unlocked or automatically retracted only after the interrogation is complete.

Figure 3:
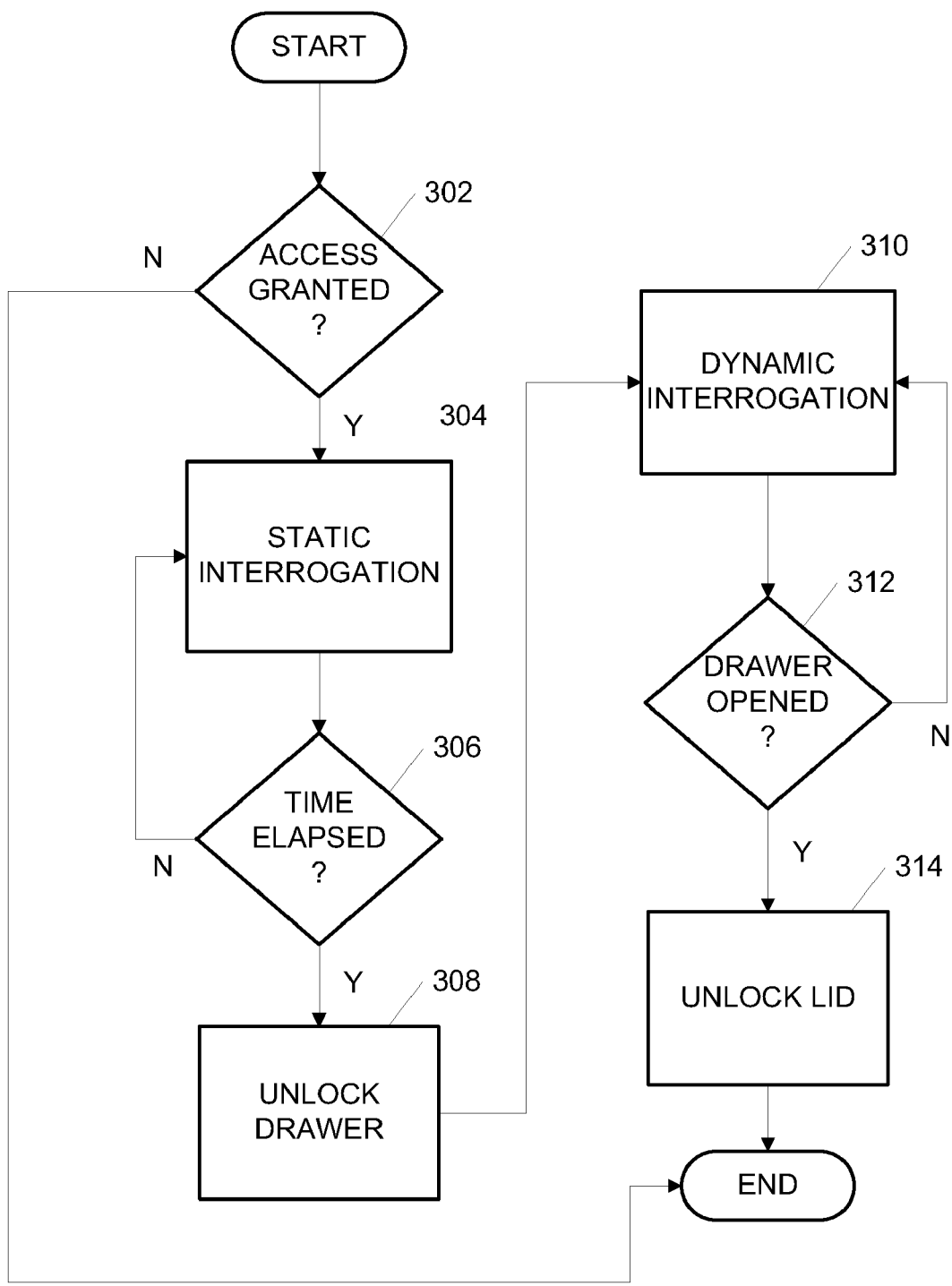
FIG. 3 is a flow chart illustrating an example dynamic read operation that occurs when a drawer included in the cabinet of FIGS. 1 and 2 is being opened in accordance with one embodiment.

FIG. 3 is a flow chart illustrating an example dynamic read operation that occurs when drawer 104 is being opened in accordance with one embodiment. First, in step 302 it is determined whether to grant access to the drawer to a requesting user. For example, if cabinet 100 includes medications, the nurse and/or doctor requesting access can be required to input identification information in order to control access to the medications. After the user is granted access to the unit, a static interrogation can be conducted while the drawer is still closed in step 304.

In certain embodiments, the static read can occur for a predetermined amount of time. Once the predetermined amount of time has elapsed, as determined in step 306, cabinet 100 can be configured to unlock drawer 104 in step 308. Once the drawer is unlocked, the user can start to draw the drawer open. While the user is drawing the drawer open, the system can continue to interrogate the drawer (dynamic interrogation) from within the cabinet in step 310 until the user successfully draws the drawer to its complete open position as determined in step 312. At this point, the system can be configured to unlock/retract the access cover (lid 106) granting the user access to the unit's contents in step 314.

Figure 4:
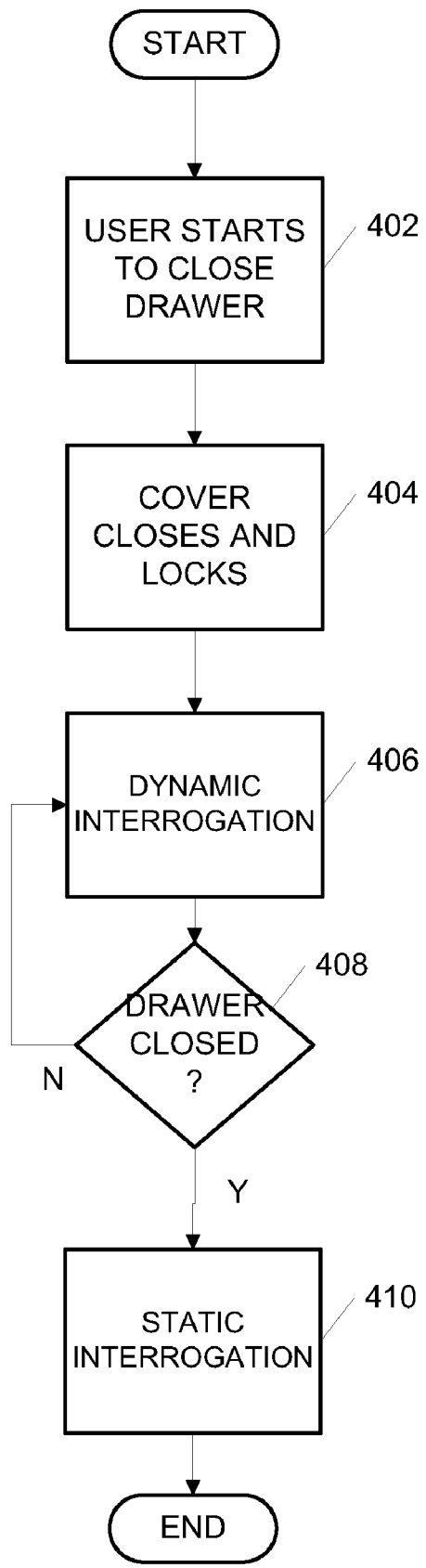
FIG. 4 is a flow chart illustrating a dynamic read operation performed while the drawer is being closed in accordance with one embodiment.

FIG. 4 is a flow chart illustrating a dynamic read operation performed while drawer 104 is being closed in accordance with one embodiment. In step 402, the user starts to close drawer 104. This can cause the system to lock and/or extend (step 404) the access cover (lid 106) to secure the contents of drawer 104 and begin a dynamic interrogation (step 406) from within the cabinet as the user continues to close the drawer. Once the drawer is completely closed, as determined in step 408, the system continues to interrogate the drawer (static interrogation) for a predetermined amount of time in step 410.

In certain embodiments, the system can employ a mechanical method of controlling the rate that the drawer is drawn open and/or closed to enhance the dynamic RFID interrogation reliability. This method can be used for example to control the quantity of tags presented to the main internal RF field, i.e., within cabinet 100, so that the rate of new tags presented to the RF field cannot exceed the interrogation read rate. For example, in certain embodiments, the open/close rate can be completely automated so that the user no longer needs to open or close the drawer. Alternatively, hydraulics, or some other system of resistance can be used to control the opening and closing rates.

In other embodiments, the system can include a drawer close delay once the access cover is locked to allow the system to initiate the RFID interrogation for a predetermined amount of time prior to the drawer closing automatically or by the user. This momentary static RFID interrogation prior to closing of the drawer allows the system to interrogate the bulk of the tags reducing the number of tags needed to be read during the dynamic read (drawer closure). This option can be considered as a "catch-up" interrogation reducing the systems overhead and increasing the system's reliability.

Figure 5:
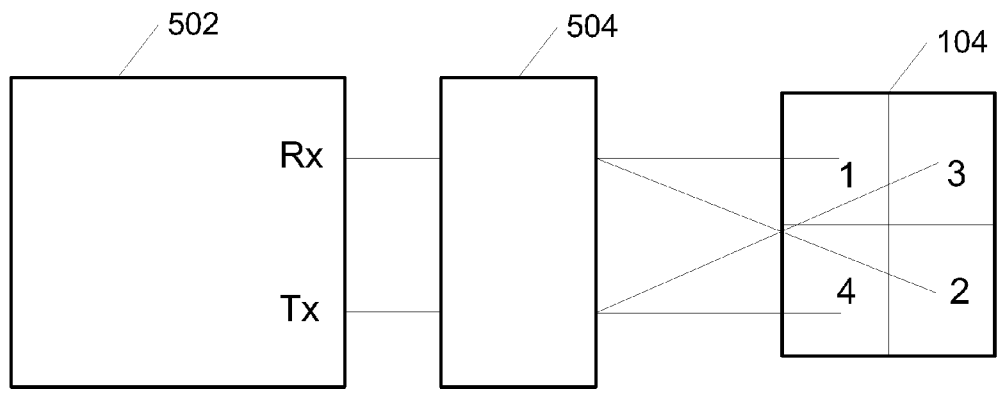
FIG. 5 is a diagram illustrating an example cabinet system, such as the system of FIGS. 1 and 2, configured to achieve successful implementation of separate transmit and receive systems.

As noted above, successful implementation of a separate transmit and receive system within the interrogation system included in cabinet 100 can be difficult to obtain, especially in the near field. Problems with conventional systems can be exacerbated as the density of items within a drawer or chamber increases. FIG. 5 is a diagram illustrating an example cabinet system 500 configured to achieve successful implementation of separate transmit and receive systems.

System 500 includes a scanner 502 with separate receive and transmit paths. These paths are ultimately coupled with antennas (not shown) configured to interrogate, e.g., the contents of a particular drawer 104. In this case, drawer 104 is divided into four chambers. Accordingly, one or more antennas (not shown) can be configured to read the contents of the four chambers. For example, in one embodiment, there are four antennas positioned so as to read the contents of the four chambers included in drawer 104. The antennas (not shown) can be coupled with a cross over switch network 504, which can be controlled so as to switch the antennas from the transmit to receive paths and vice versa as needed.

It will be understood that scanner 502 and cross over switch network 504 can be included on or within cabinet 100, and that the illustration of FIG. 5 is for convenience only.

A goal of a cabinet application can be to maintain an extremely high tag density by containing the RF field within a conductive chamber resulting in a high RF power density. A significant issue is then reflections from the conductive chamber reflect back into the scanner's receive path, which reduces the system's receive sensitivity. Another problem is that the tagged item typically ends up in the antenna near field, detuning the antenna, and further decreasing the systems receive sensitivity.

In the system of FIG. 5, separate transmit and receive paths are employed to overcome such issues. In the system of FIG. 5, any antenna (not shown) in the system can be dynamically reconfigurable using cross over network 504 to act as a transmit or receive antenna as needed. By switching the antenna configurations, maximum transmit and receive capabilities can be achieved.

Table 1 illustrates eight example combinations for the above example system configuration:

TABLE 1

| Antenna Configuration | Antenna | |
| --- | --- | --- |
| | Tx | Rx |
| 0 | 1 | 3 |
| 1 | 1 | 4 |
| 2 | 2 | 3 |
| 3 | 2 | 4 |
| 4 | 3 | 1 |
| 5 | 3 | 2 |
| 6 | 4 | 1 |
| 7 | 4 | 2 |

Thus, as can be seen, in configuration 0, antenna 1 can be configured under the control of scanner 502 as a transmit antenna, while antenna 3 is configured as a receive antenna; in configuration 1, antenna 1 is a transmit antenna and antenna 4 is a receive antenna; in configuration 2, antenna 2 is a transmit antenna and antenna 3 is a receive antenna; and so on.

In this manner, more accurate interrogations of all the items within drawer 104 can be achieved by rotating the transmit and receive functions between the different antennas in different combinations. Thus for example, while transmit signals are being transmitted by antenna 1 in configuration 0, return signals are being picked up by antenna 3. In configuration 1, antenna 3 is used to try and pick up return signals initiated by signals transmitted via antenna 1. It will be understood that some of the signals picked up by antenna 3 in configuration 1, would not have been picked up by antenna 4 in configuration 0 and vice versa. Thus, greater receive coverage is obtained.

Moreover, if antenna 1 is used for both transmit and receive, then reflections from the conductive chamber will reflect back into the scanner's receive path, which reduces the system's receive sensitivity. This is the problem with conventional systems.

In another embodiment, separate transmit and receive paths can be used with static antenna designations, as opposed to the dynamic configurations of FIG. 5. In such embodiments, receive antennas can be placed in strategic locations within the chamber that provide the best isolation from the transmit antennas. In this manner better reception of the tag responses can be achieved.

Figure 6:
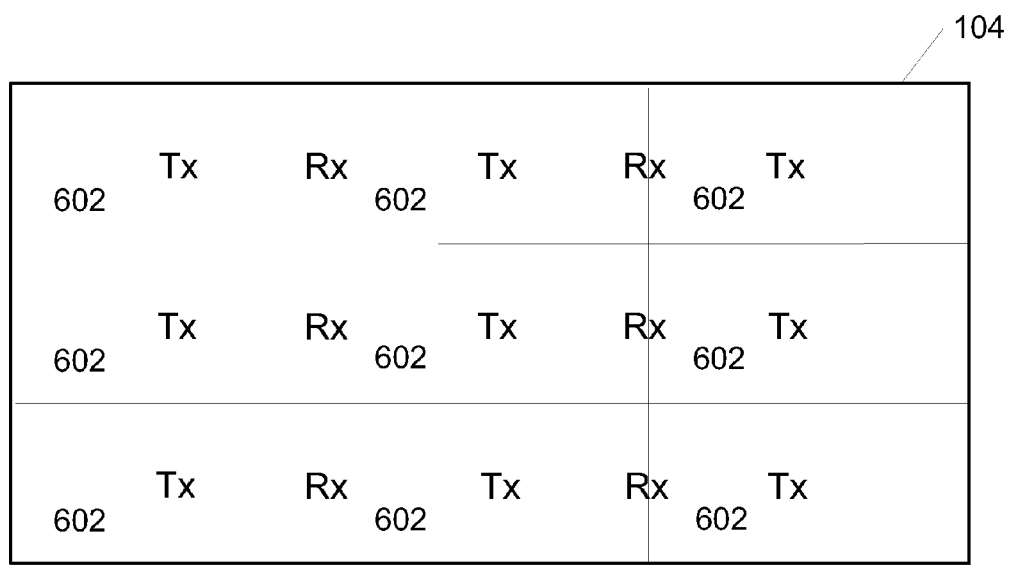
FIG. 6 is a diagram illustrating an example embodiment of a cabinet system, such as the system of FIGS. 1 and 2, that employs strategic antenna placement in accordance with one embodiment.

FIG. 6 is a diagram illustrating an example embodiment of a cabinet system that employs such strategic antenna placement. In the example of FIG. 6, receive antennas are designated as Rx and transmit antennas as Tx. FIG. 6 illustrates the placement of the antennas relative to a drawer 104 that comprises a plurality of chamber 602.

In the example of FIG. 6, Rx antennas have been strategically placed to ensure maximum receive capabilities. For example, a static tag can rest between two Tx antennas reducing the amount of power available to that tag. In this situation, the tag is capable of turning on and participating in the interrogation, however the faint response from the tag cannot necessarily be detected by the scanner if the Tx antennas are also used for receiving, resulting in a failed interrogation. Here, however, the Rx antennas are located between the Tx antennas reducing the path losses and increasing the tag response magnitude present to the Rx antennas and ultimately the scanner receiver resulting in a successful interrogation.

Figure 7:
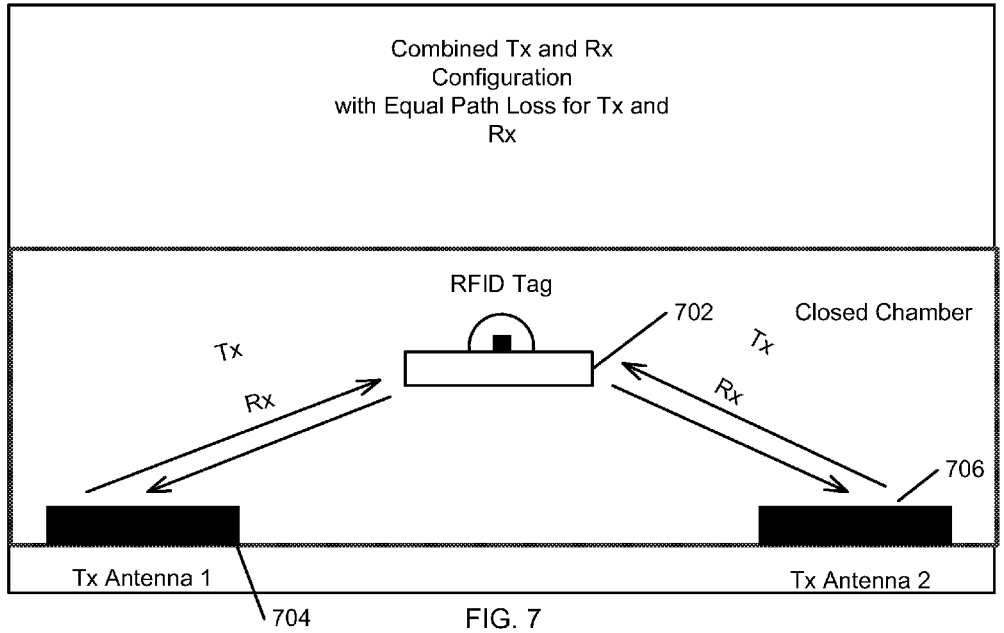
FIGS. 7 and 8 illustrate further views of a system with and without a central Rx antenna as illustrated and described with respect to FIG. 6.
Figure 8:
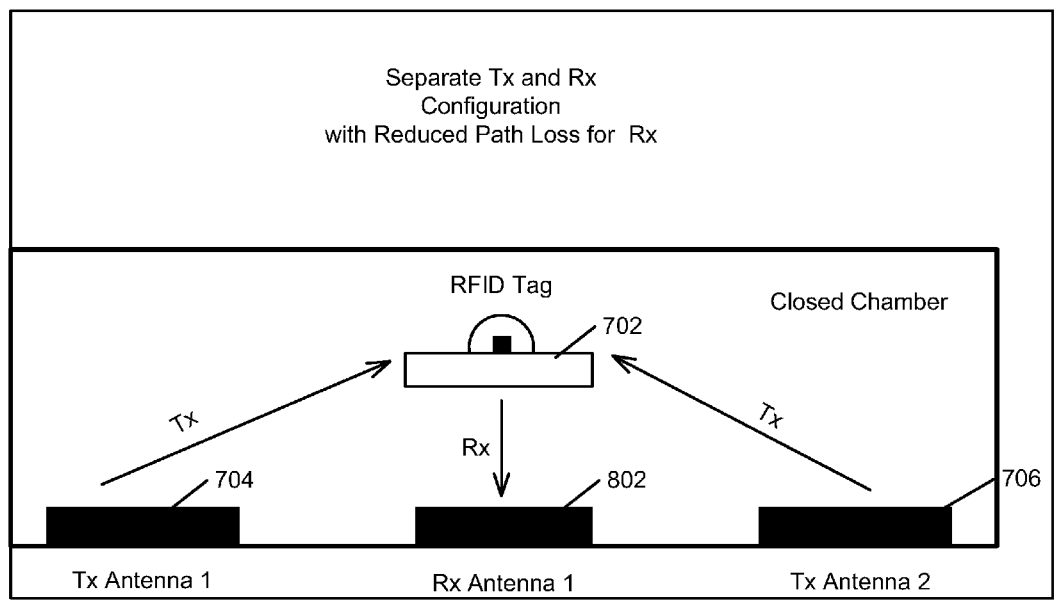

FIGS. 7 and 8 illustrate further views of a system with and without a central Rx antenna as illustrated and described with respect to FIG. 6. As can be seen in the example of FIG. 8, including the additional receive antenna reduces the return path, and therefore path loss, for tags residing between the Tx antennas.

It should be noted that the embodiments of FIGS. 5 and 6 can be implemented in combination to obtain further advantages.

The successful implementation of a real-time item management cabinet 100 can depend on several factors. Such a cabinet implementation can take on several form factors to meet the end users needs; however, certain components can be included in order to ensure optimum capability in accordance with the systems and methods described herein.

Figure 9:
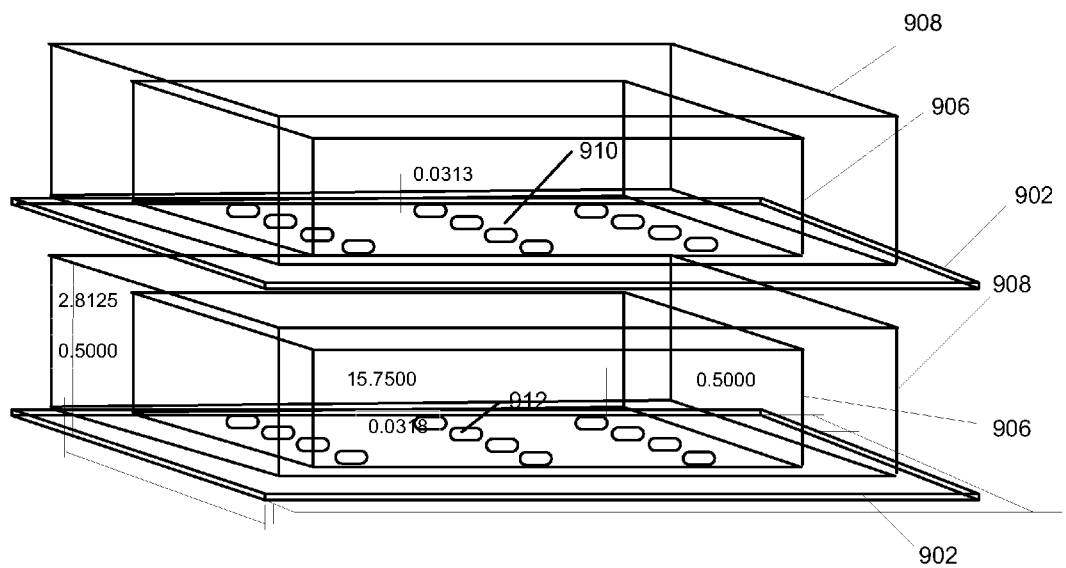
FIG. 9 is a diagram illustrating the cabinet of FIGS. 1 and 2 in more detail.

FIG. 9 is a diagram illustrating a cabinet 100 in more detail. First, cabinet 100 can comprise one or more chambers that are RFID enabled. In this case, the term chamber is meant to refer to areas 904 within cabinet structure 102 as opposed to within a drawer 104. It will be understood, however, that each chamber 904 can house a drawer 104. Alternatively, one or more of chambers 904 can include a rigid shelf as opposed to a drawer. The premise of the cabinet concept is that a RFID tag is placed on the item to be tracked and then the item is placed into the cabinet. Items can be randomly placed into the cabinet or discipline can be used in placing the items.

Once all the contents of the cabinet have a RFID tag, the system is ready to conduct automatic inventory, e.g., as describe above, every time the unit is accessed by a user. Access of the unit can be controlled by mechanical lock connected to a host system or any other access control device such as a contactless key. Further, various levels of security can be implemented by granting access to only certain chambers, to only certain users, or some combination thereof.

Cabinet 100 can comprise antenna array panels 902 on which Rx/Tx antennas 912 are arrayed for interrogating the tagged items. In the example of FIG. 9, there is one panel 902 per chamber 904. Antennas 912 can be arrayed and/or configured as described with respect to FIGS. 5-8.

Chambers 904 can comprise inner (906) and outer (908) walls. For example, outer walls 908 can comprise a conductive material to maintain high field strength and generate specific modes. For example, chamber walls 908 can include metalized film or perforated metal, e.g., to contain the RF energy and allow light through simultaneously so that the chamber contents are visible.

Each chamber 904 can also comprise a non conductive, false inner wall 906 to prevent the RFID tags from contacting the conductive outer walls 908 causing them to short and/or detune. The distance between the non conductive false wall 906 and the conductive outer wall 908 should be no less than lA the RF wave length. Similarly, each chamber 904 can include a shelf 910 comprising a non-conductive surface to prevent shorting and/or detuning of the RFID tags.

The dimensions of each chamber 904 can be configured to resonate at a given frequency of the RFID system resulting in maximum field strength within the chamber. This is described in more detail below.

Cabinet 100 can include an antenna system that uses both Right Hand Circular Polarization (RHCP) and Left Hand Circular Polarization (LHCP) to eliminate exciting non-active antennas on opposing parallel planes resulting in disrupted RF fields. LHCP or RHCP antennas are used on a single plane of antenna, e.g., panels 902, to improve return loss from the first reflected signal from the opposing wall.

In certain embodiments, the scanner can be configured to receive signals over multiple frequencies in order to increase the reception capabilities. For example, due to the nature of passive RFID, reception of a tags back scatter signal on the carrier frequency can be extremely challenging when radiating into a closed chamber such as a chamber 904. Allowing the receiver to listen on one or multiple harmonics of the carrier frequency can aid the system's reception capability in a closed chamber environment. This is also described in more detail below.

Further, multiple radiating elements 912 can be used within a closed chamber 904 to facilitate the reading of items as the items themselves will disrupt the RF field. This is known as RF field diversity. As is understood, there are many types of diversity, including filed diversity, spatial diversity, time diversity, polarity diversity, etc., and that in general diversity can help improve the performance of wireless communication systems. Thus, in the example of FIG. 9, the diversity that can be achieved due to the use of multiple antenna elements 912 can improve the overall system performance. Especially when combined with the methods described above.

As noted above, a RFID cabinet systems, such as system 100, typically uses the electric field component of the RF signal to communicate with the beam powered RFID tags. Depending on frequency used, some frequencies can be greatly attenuated by liquid items within the cabinet resulting in failed interrogation due to insufficient field strength. Accordingly, in certain embodiments the magnetic component of the RF signal is primarily used for situations where a large amount of liquid is present in the chamber to facilitate the interrogation of an RFID tag. For example a large IV bag pre-filled with a solution and tagged with an RFID inlay can be stored in cabinet 100. In this situation, a standard electric field optimized RFID tag will not be easily read due to the electric field absorption by liquid at a give frequency.

By employing a hybrid antenna system for the scanner antenna and/or the tag antenna, the system is capable of taking advantage of the extended read range of the electric field and the magnetic field's ease of penetrating large volumes of liquid. Thus, in certain embodiments, a chamber 904 can include a combination of standard electromagnet antennas 912, the primary function of which is to interrogate standard tags optimized for the electric field, as well as one or more loop antennas (not shown) designed for tags that are optimized for magnetic coupling. Items that include a large amount of liquid can then be tagged with tags optimized for magnetic coupling. For example, a 500 mL bag of blood can be tagged with tags optimized for magnetic coupling. Whereas a pill package for example can be tagged with an electric field optimized tag. Both the blood bag and pill package can reside inside a chamber 904 and each can be effectively interrogated with its corresponding scanner antenna.

In certain embodiments, chamber 904 can be configured with antennas that are efficient in both the electric field and magnetic field. Thus, a reduced number of antennas can be used for both electric field and magnetic field reads. Similarly, the RFID tags can also be designed so that they are efficient in both the magnetic field and electric field. Thus, one RFID tag can serve dual purpose for both large liquid volume and low liquid volume.

Also as noted above, tags can comprise an effective area that is much larger then the real area and is normally at least 1A wavelength of the frequency being used. Since RFID tags are typically place on various items that can greatly reduce the tags efficiency due to intrusion of its effective area, applications that do not adhere to any item discipline can result in poor read performance, because other items can come into contact or near contact with the RFID tag causing further efficiency reductions.

Thus, in certain embodiments the RFID tag can be transformed into a larger form factor that is the same size as the effective area of the tag. This can help reduce, or prevent the reductions in efficiency inherent in many cabinet applications. The tag can, for example, be transformed by encapsulating it in a material that will not detune the RFID tag, e.g., foam. The increased form factor, and careful selection of material can eliminate the possibility of any item detuning the RFID tags by encroaching it's effective area.

Figure 10A:
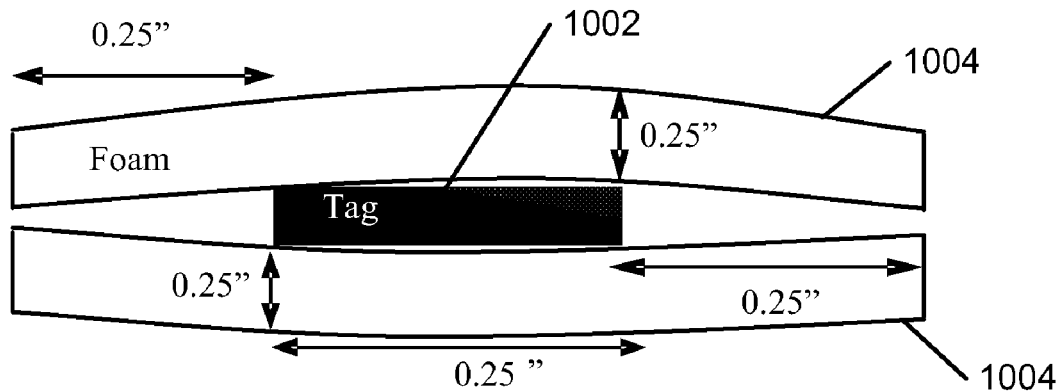
FIGS. 10A and 10B are diagrams illustrating an example embodiment of a RFID tag that has been encapsulated in material in order to increase the tags effective area.
Figure 10B:
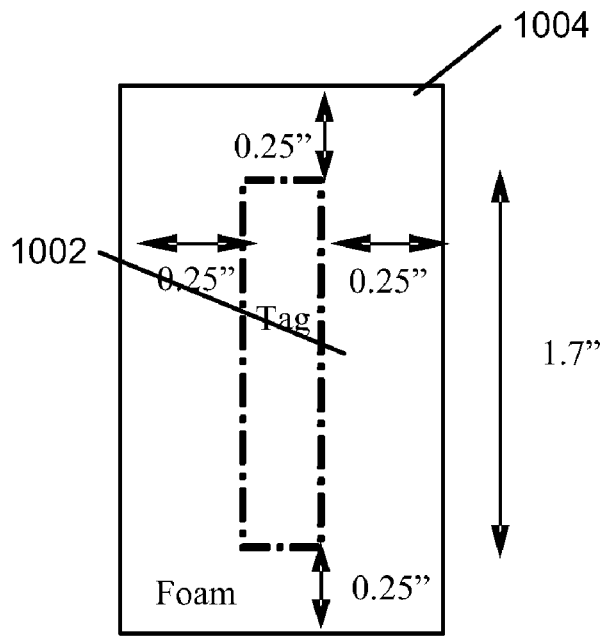

This is illustrated in FIGS. 10A and 10B. As can be seen in FIG. 10A, layers 1004 and 1006 of, in this case, foam material can be placed around tag 1002 in order to increase the effective area of the tag an prevent the tag from being detuned by nearby items. In this case, the length of tag 1002 is equivalent to a quarter wavelength of the RF signals being transmitted and received by tag 1002. Thus, layers 1004 and 1006 can be configured to extend the same distance all around tag 1002 as illustrated in FIGS. 10A and 10B.

Also as noted above, RF signal propagation in contained environments is not well defined, with huge amplitude variations in resonant versus null locations within a chamber. When RFID tags are placed in the chamber's null locations, the tags are not powered and cannot be read, which ultimately causes failures. Accordingly, in certain embodiments, chamber 904 can be configured so that it is in resonance with the RF frequency being used. The resonance and resonance mode can be controlled by, for instance but not limited to, using metal enclosure with certain dimension, placing absorbers within the chamber, and/or strategically selecting the positions of antenna 912. In this manner, the overall RF field distribution within a given cavity, or chamber, can be maintained at a high RF energy level and predictable distribution in the area.

A single antenna can be used in such a resonance mode; however, in case a single antenna or radiator cannot provide sufficient coverage, multiple radiators can be sequentially activated either one at a time or multiple at a time to provide different resonance patterns, the combination of which will provide uniform RF energy distribution. When all the resonance patterns are viewed in total, the composite RF levels, will be sufficient to energize a passive RFID tag positioned anywhere within the chamber.

Further, in some embodiments, gaps are included in the design of chamber 904. Using properly sized and spaced cavity openings, or gaps, will aid in creating cavity resonances with an evenly distributed RF field. Similarly, properly sized and spaced RF absorber can be used for the same function.

Even with optimal distribution of the RF field, there may be occasions where a certain RFID tag does not receive sufficient field strength. This may be due to changes induced with the addition of multiple RFID tags, or the product which the tag resides upon. In these situations, slight variation of the cavity is sufficient to alternate the resonance and provide sufficient field strength to the previously undetectable tag. A method of varying the cavity is to begin scanning for RFID tags prior to the chamber door or drawer being closed and after the door or drawer has been opened. Scanning while the cavity is in a state of transition will provide additional variation to the field. Thus, the dynamic read process described above, or something similar, can also be used to vary the cavity.

Position sensors on the door or drawer can be used to provide indications of when to initiate and when to terminate such dynamic reading or scanning A drawer lid 106, with position indication, can be used to safeguard against items being removed from the drawer as it is withdrawn from or pushed into a chamber 904.

In other embodiments, interference avoidance between transmit and receive signals in a chamber can be achieved though the use of a fundamental signal in the downlink path (scanner to tag), and a harmonic signal in the uplink path (tag to scanner). The RFID tag generates harmonic RF energy when communicating data back to the RFID scanner. The RFID scanner is capable of receiving harmonic RF energy from the passive RFID tag, instead of only backscatter energy at the fundamental, or transmitted, frequency. This method provides a means for improved system sensitivity by avoiding the need to simultaneously transmit and receive on a common frequency.

Figure 11:
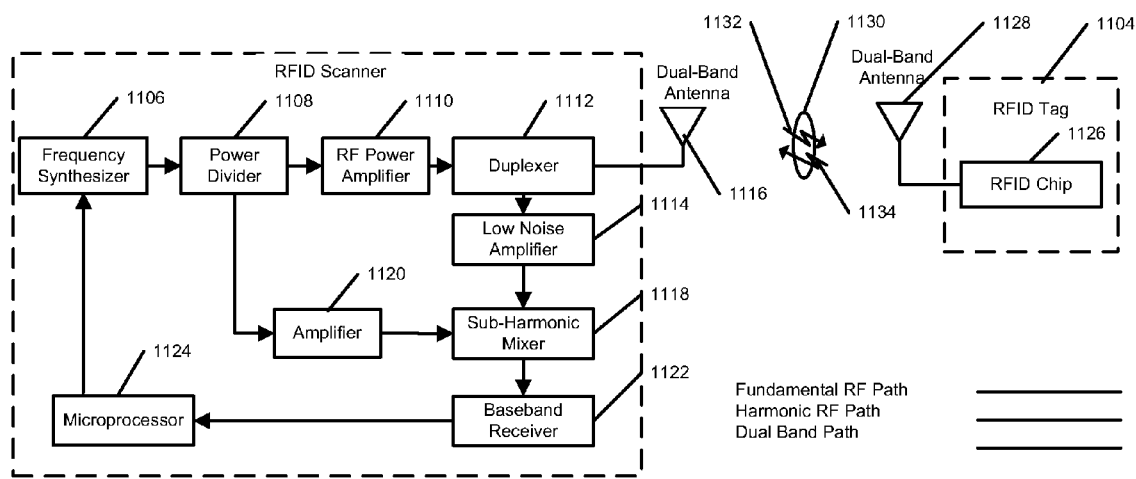
FIG. 11 is a diagram illustrating an RFID system 1100 that uses a harmonic in the uplink in accordance with one embodiment.

FIG. 11 is a diagram illustrating an RFID system 1100 that uses a harmonic in the uplink in accordance with one embodiment. For example, the system of FIG. 11 can be implemented in a cabinet application such as illustrated in FIG. 1 and in more detail in FIG. 9. As can be seen, system 1100 comprises a scanner 1102 and a tag 1104. Scanner 1102 is configured to transmit and receive RF signals 1130 via antenna 1116. Received signals are shunted via duplexer 1112 to a receive path comprising Low Noise Amplifier (LNA) 1114, configured to amplify the typically low level received signals while adding as little noise as possible to the amplified received signal, sub-harmonic mixer, configured to remove the harmonic carrier frequency of the received signal and finally baseband processor 1122, configured to recover any information included on the received signal. For example, baseband process can comprise the filters and Analog-to-Digital (D/A) converters necessary to convert the information into data that can be processed by processor 1124.

Scanner 1102 also comprises a transmit path comprising microprocessor 1124, which can generate an information signal for transmission to tag 1104. The information signal can be used to control frequency synthesizer 1106 in order to generate a transmit signal at the fundamental frequency. Power divider 1108 can siphon a small amount of power from the transmit signal for use, after amplification by amplifier 1120, by sub-harmonic mixer 1118. The path through amplifier 1120 can be referred to as the LO generation path. RF power amplifier 1110 can then amplify the transmit signal to a sufficient level for transmission to tag 1104 and duplexer 1112 can shunt the transmit signal to antenna 1132 for transmission while preventing the transmit signal from entering the receive path.

As noted synthesizer 1106 is configured to generate the fundamental RF signal for downlink 1132. RFID tag 1104 receives the fundamental signal, which provides power and data to the tag. In uplink path 1134, RFID tag 1126 creates short bursts of harmonic signal when providing data back to RFID scanner 1102.

In certain embodiments, sub-harmonic mixer 1118 can be replaced with a frequency doubler, an amplifier and standard mixer. Cost and performance will dictate the actual design.

Duplexer 1112 is required in order to prevent receive signals form entering the transmit path and vice versa. Because the frequency of signals on the uplink 1134 are different than the frequency used for the downlink 1132, conventional duplexer technology can be used to separate and isolate the two at the antenna port. It should also be noted that both scanner 1104 and tag 1102 require dual-band antennas 1116 and 1128 respectively, in order to optimally transmit and receive signals at the fundamental and harmonic frequencies.

Some of the embodiments above disclose the use of separate transmit and receive antennas. As both transmit and receive antennas are operating in a closed chamber, in such embodiments, the isolation between transmit and receive antennas can be poor. In other words, because the transmit and receive antennas are positioned in a closely confined space, a strong transmit signal from the scanner can leak into the scanner receiver through a receive antenna. In normal conditions, the scanner receiver is able to suppress the leakage (for example by filtering) so that the residual leakage is negligible comparing to the desired backscattered signal from tags. However, if this leakage exceeds the receiver suppression capability, the residual leakage will be added to the desired signal so that the scanner receiver will make false decisions on what it actually received from tags.

Figure 12:
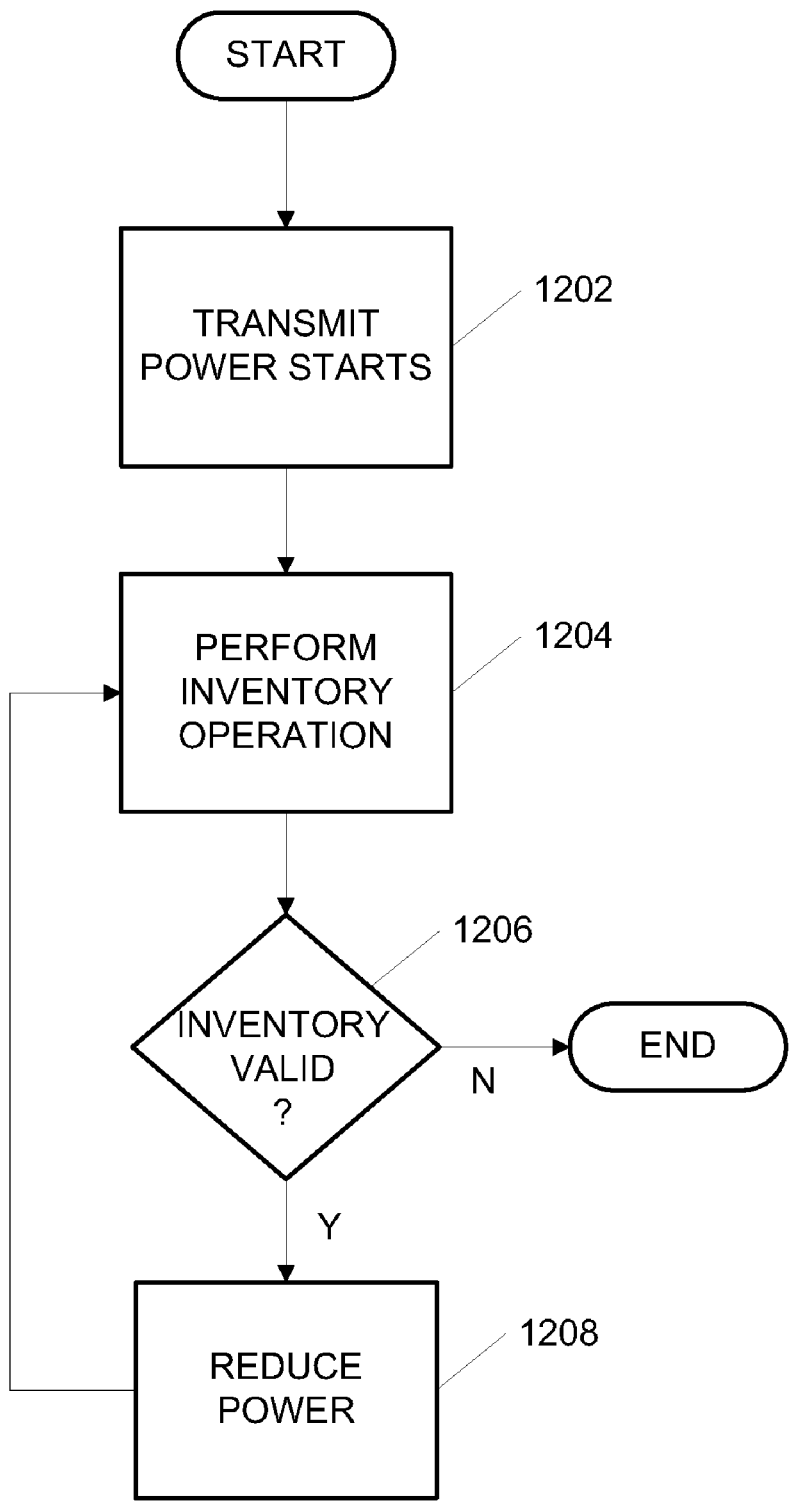
FIG. 12 is a flow chart illustrating an example method for reducing transmit power in order to prevent leakage into a receive antenna in accordance with one embodiment.

In certain embodiments, the scanner transmit power in strategically reduced to alleviate the problem described above. For example, in one embodiment a fixed reduction process can be used as illustrated in the flow chart of FIG. 12. First, in step 1202, the scanner can be configured to transmit power starts with the maximum allowable power. In step 1204, the scanner can perform an inventory operation, i.e., send interrogation signals and receive responses from tagged items within a drawer/chamber, at this maximum power setting. In step 1208, the scanner power is reduced by a certain amount, for example 2 dB, and the scanner performs the inventory operation of step 1204 again. After the initial power reduction, it can be determined in step 1206 whether the inventory results obtained with the lower power are still valid. If so, then the power can be reduced in step 1208 again and the inventory taken again in step 1204.

Once it is determined in step 1206 that the inventory results are not valid, i.e., certain items detected in the previous inventory (step 1204) are no longer detected, then the process can end and the new power level can be used for future operations. In this manner a minimum useable power level can be maintained that should eliminate or reduce any leakage into the receive antenna.

Figure 13:
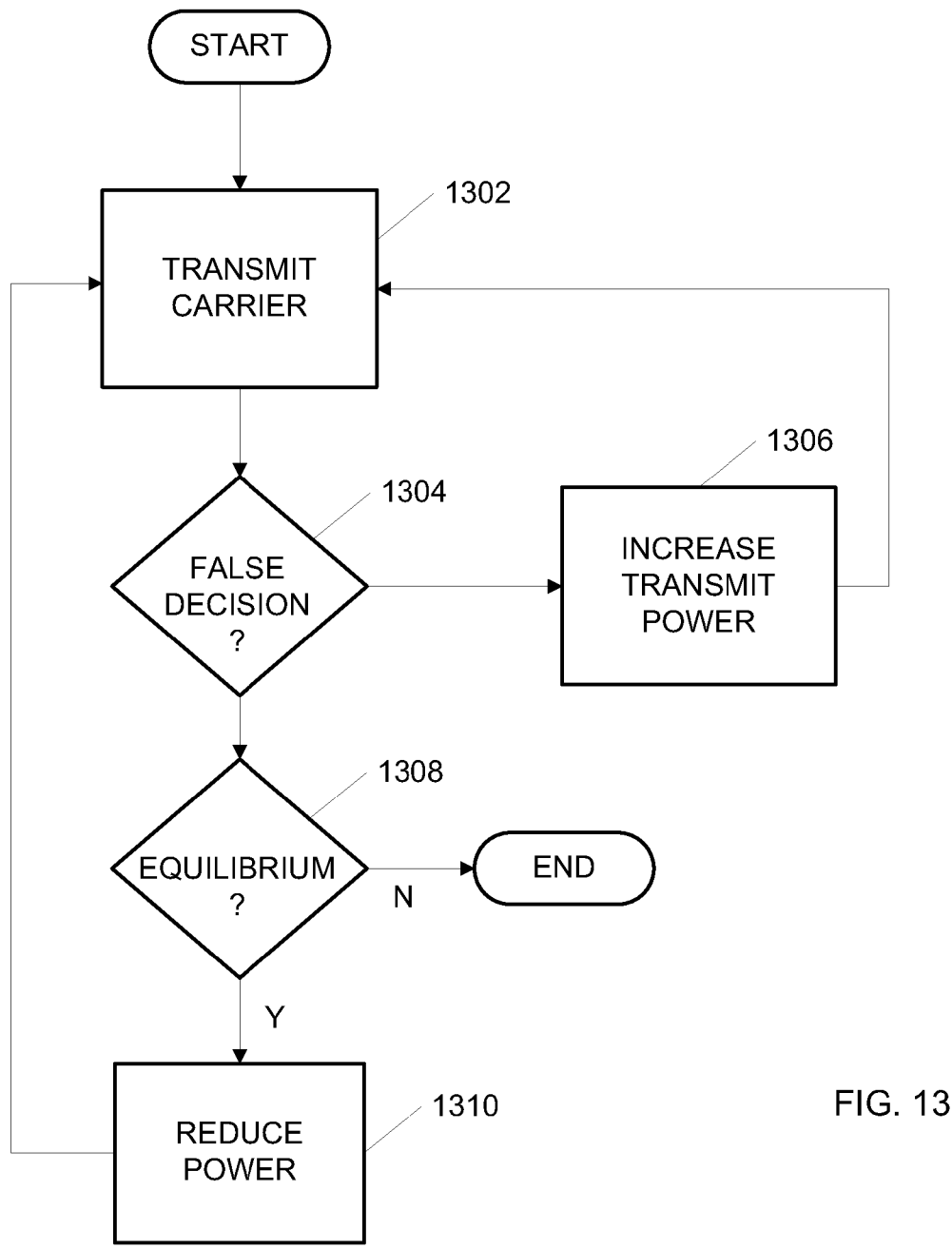
FIG. 13 is a flow chart illustrating an example method for reducing transmit power in order to prevent leakage into a receive antenna in accordance with another embodiment.

In another embodiment, an adaptive reduction process can be used as illustrated in the flow chart of FIG. 13. The adaptive method allows the scanner receiver to determine if any unwanted leakage is excessive. If the scanner receiver senses an excessive unwanted leakage, it will reduce the transmit power gradually until a minimum transmit power is reached. If the scanner senses the leakage is not excessive, then the scanner will increase its transmit power gradually until the maximum transmit power is reached.

For example, in step 1302 the scanner can transmit a carrier or a preset training signal to which the tags are programmed not to respond. If the scanner receiver makes false decisions, as determined in step 1304, i.e., the scanner detects a tag response, then an excessive unwanted leakage is present, and the scanner can be configured to reduce its transmit power in step 1310 and try again. If the scanner does not make false decisions, then the scanner can be configured to increase its transmit power in step 1306 and try again. At some point it will be determined that the optimal transmit power has been achieved (step 1308) and the process will end.

While certain embodiments of the inventions have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed is:

1. A method for performing a dynamic scan operation in a Radio Frequency Identification (RFID) cabinet that includes a cabinet structure, a drawer configured to slide in and out of the cabinet structure, the drawer configured to hold RFID tagged items, and a scanner, the method comprising:

receiving, at the scanner, a request for access to the drawer;

performing, at the scanner, a scan of the RFID tagged items before the drawer is removed;

releasing the drawer from the cabinet after a predetermined period of time;

continuing to scan, at the scanner, the RFID tagged items as the drawer is removed; and unlocking an access cover of the drawer after the drawer has been moved to a predetermined location.

2. The method of claim 1, further comprising detecting, at the scanner, when the drawer is to be closed and scanning, at the scanner, the RFID tagged items as the drawer is closed.

3. The method of claim 2, further comprising detecting, at the scanner, when the drawer is closed and continuing to scan, at the scanner, the RFID tagged items for a predetermined period of time.

4. The method of claim 1, wherein the method further comprises detecting, at the scanner, when the drawer is going to be closed based on the access cover being locked or closed over the drawer.

5. The method of claim 1, further comprising stopping scanning, at the scanner, once the drawer reaches a complete open position.

6. The method of claim 1, further comprising detecting, at the scanner, when the drawer is to be removed.

7. The method of claim 6, further comprising beginning to scan, at the scanner, responsive to detecting that the drawer is to be removed.

8. The method of claim 6, wherein the step of continuing to scan is performed responsive to detecting that the drawer is to be removed.

9. A method for performing a scan operation in a Radio Frequency Identification (RFID) cabinet that includes a cabinet structure, a drawer configured to slide in and out of the cabinet structure, the drawer configured to hold RFID tagged items, and a scanner, the method comprising:

generating a transmit signal comprising a maximum allowable power;

interrogating the RFID tagged items via the plurality of antenna using the transmit signal;

receiving responses via the plurality of antenna from the RFID tagged items in response to the transmit signal;

reducing the power of the transmit signal;

interrogating the RFID tagged items via the plurality of antenna using the transmit signal with reduced power;

receiving responses via the plurality of antenna from the RFID tagged items in response to the transmit signal with reduced power;

determining whether the responses to the transmit signal with reduced power are valid; and when it is determined that the responses are valid, then repeating the steps until the responses are invalid.

* * * * *